United States Patent [19]
Hamilton et al.

[11] Patent Number: 5,314,492
[45] Date of Patent: May 24, 1994

[54] COMPOSITE PROSTHESIS

[75] Inventors: John V. Hamilton, Foxborough; Salvatore Caldarise, Hanson; Debra J. Treacy, Middleborough, all of Mass.

[73] Assignee: Johnson & Johnson Orthopaedics, Inc., Raynham, Mass.

[21] Appl. No.: 881,105

[22] Filed: May 11, 1992

[51] Int. Cl.$^5$ .............................................. A61F 2/32
[52] U.S. Cl. ........................................ 623/23; 623/16
[58] Field of Search ...................... 623/11, 16, 18, 20, 623/21, 23, 66

[56] References Cited

U.S. PATENT DOCUMENTS

| | | | |
|---|---|---|---|
| 3,623,164 | 11/1971 | Boknos | 623/16 |
| 4,662,887 | 5/1987 | Turner et al. | 623/16 |
| 4,892,552 | 1/1990 | Ainsworth et al. | 623/23 |
| 4,902,297 | 2/1990 | Devanathan | 623/16 |
| 4,978,358 | 12/1990 | Bobyn | 623/23 |
| 4,978,360 | 12/1990 | Devanathan | 623/66 |

FOREIGN PATENT DOCUMENTS

| | | | |
|---|---|---|---|
| 0277727 | 8/1988 | European Pat. Off. | A61L 27/00 |
| WO91/18562 | 12/1991 | PCT Int'l Appl. | A61F 2/36 |
| WO91/18563 | 12/1991 | PCT Int'l Appl. | A61F 2/36 |
| 2216425 | 10/1989 | United Kingdom | A61F 2/28 |

OTHER PUBLICATIONS

Current Inderdisiplinary Res. 1985, pp. 371-376, M. Perren, et al.
NASA Tech Briefs, Mar. 1992, pp. 85 & 86.

*Primary Examiner*—David Isabella
*Attorney, Agent, or Firm*—Michael Q. Tatlow

[57] ABSTRACT

A composite stem for a prosthesis, particularly a hip prosthesis, including a metal core and a fiber reinforced composite shell surrounding the core to provide modulus values that are similar to bone. The composite shell is preferably composed of braided fibers and a thermoplastic resin. The stiffness of the prosthesis can be varied along the length of the stem. The metal core contributing between 5 and 25 percent of the total flexural stiffness of the stem.

14 Claims, 6 Drawing Sheets

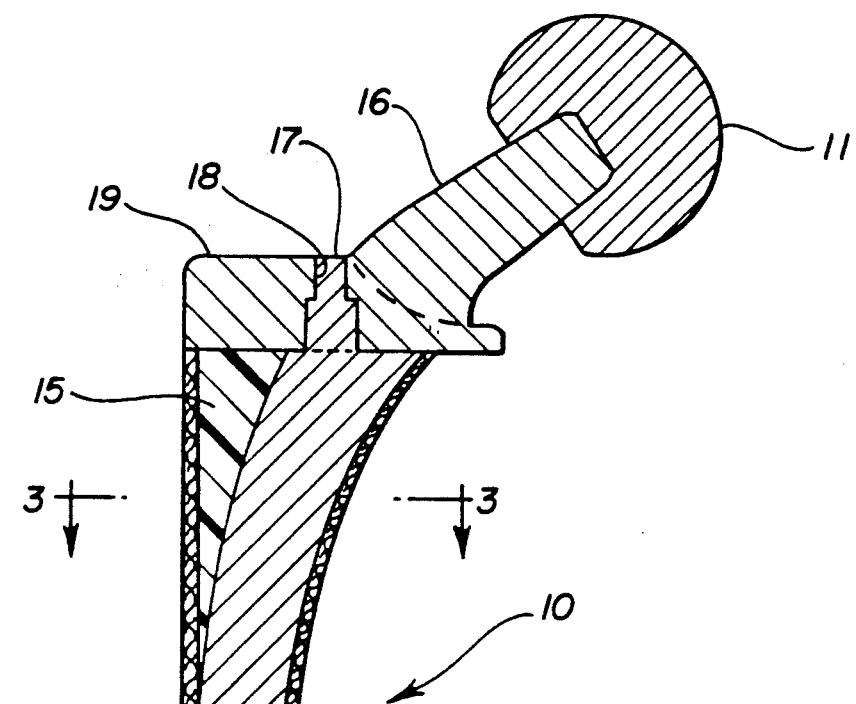
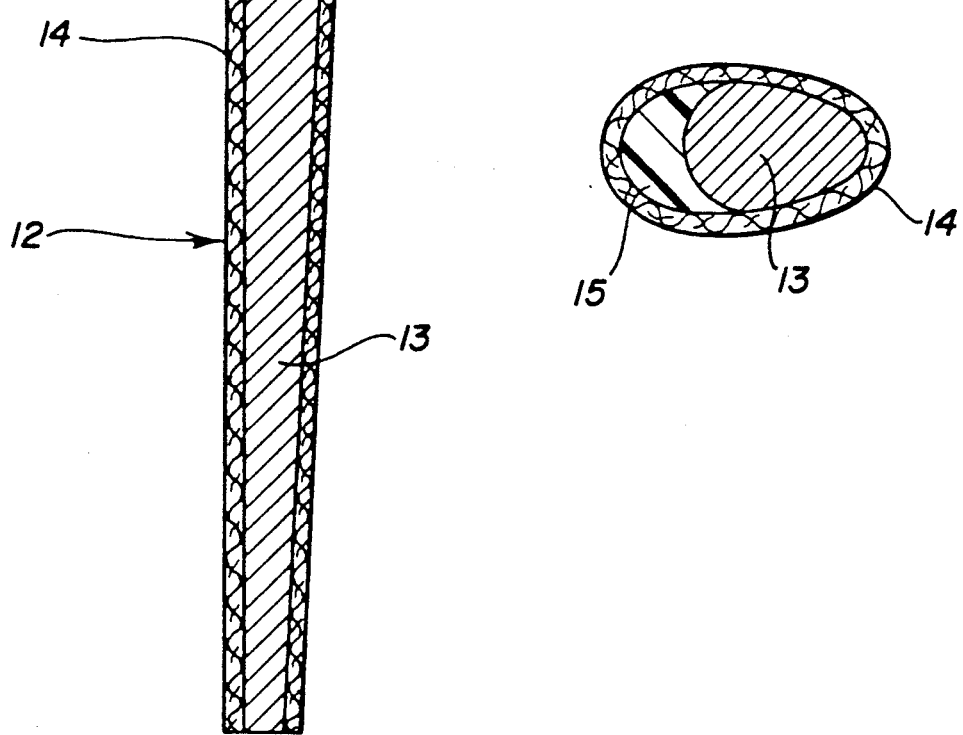

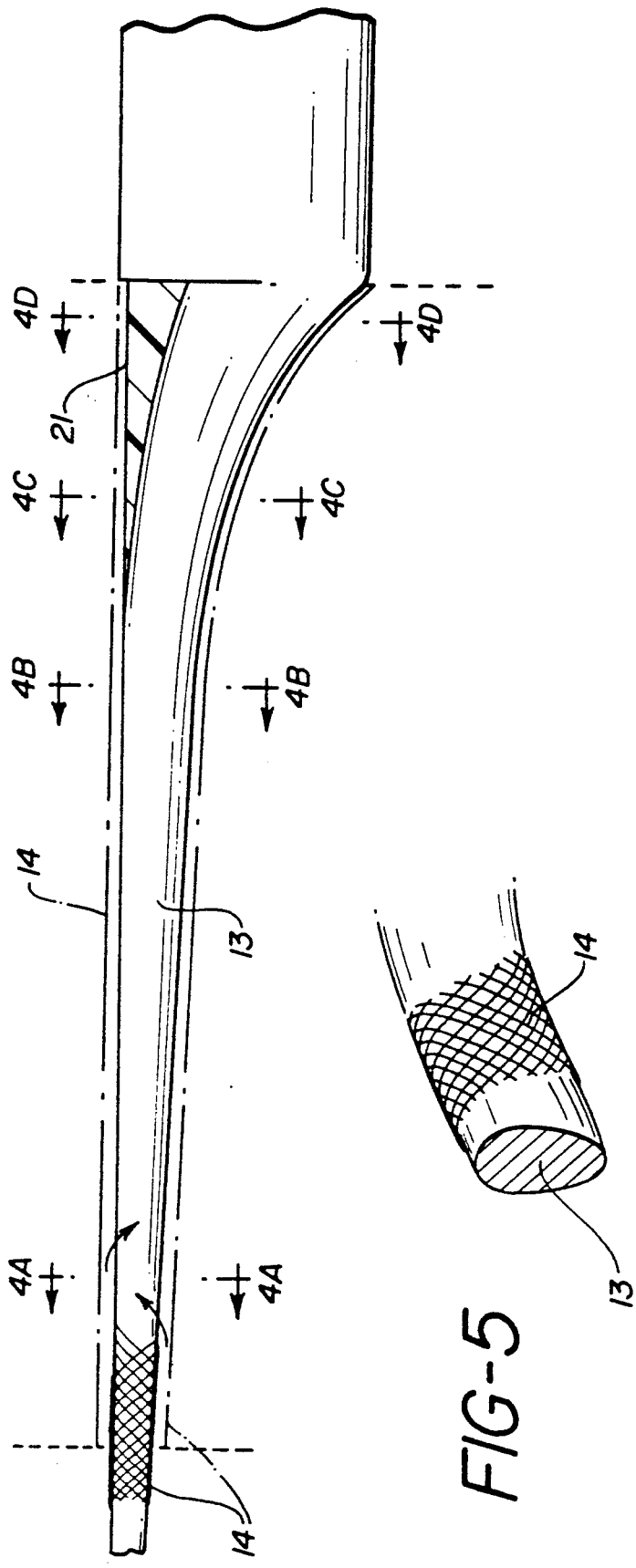

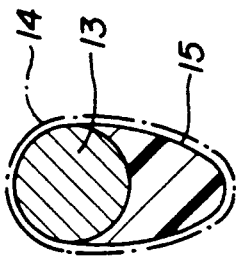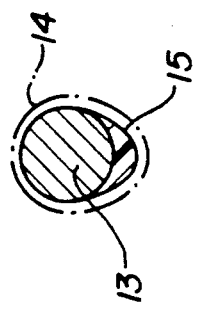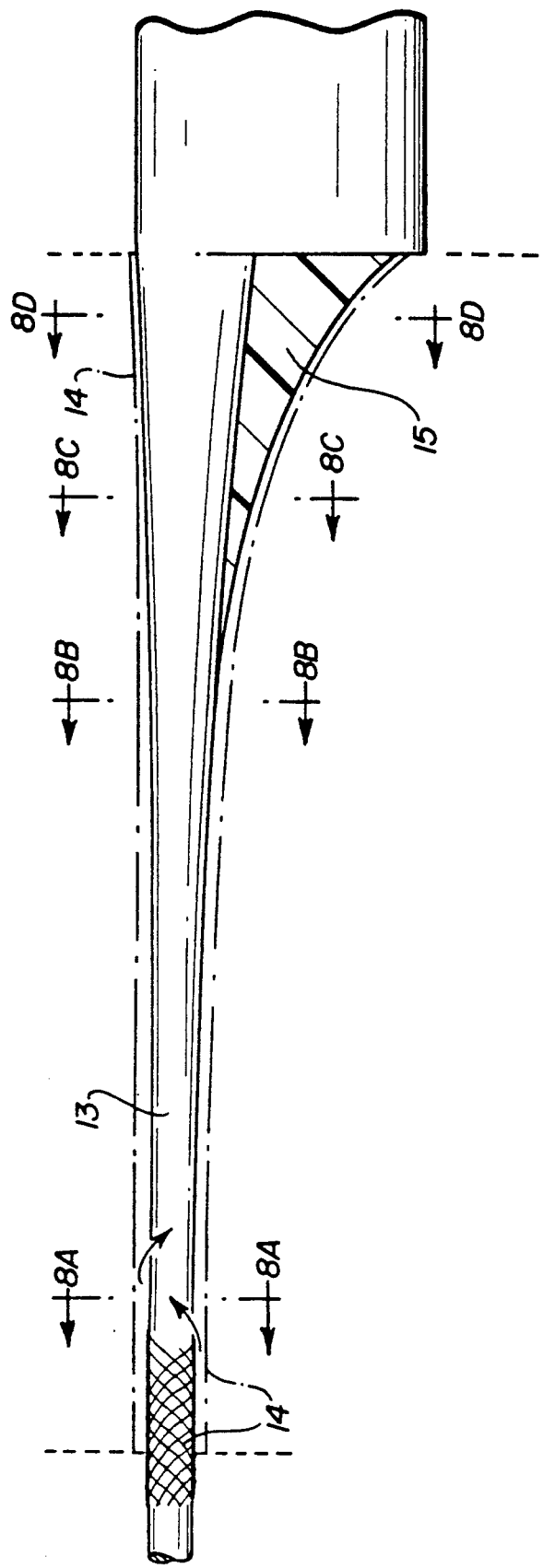

COMPOSITE PROSTHESIS

FIELD OF THE INVENTION

The present invention relates to a composite structure that is particularly suitable for use as a component of an artificial joint prosthesis and more particularly to a component having a shaft or stem that is to be inserted into a cavity in a bone such as the femoral component of a hip prosthesis, the tibial component of a knee prosthesis, the glenoid component of a shoulder prosthesis and an elbow prosthesis.

BACKGROUND OF THE INVENTION

The role of the hip joint in the skeletal system is to transmit loads between the pelvis and the femur and allow for motion between the two such that normal activities such as walking and stair climbing can occur. The loads are transmitted through a joint similar to a ball and socket joint. The head of the femur provides the ball portion of this joint. Its role is to provide a mode of transmitting the axial, torsional and bending forces that are developed during normal human activities. The structure of a normal femur is a tubular construction in which the wall (or cortical shell of the femur) carries most of the load and the load is transmitted from the femoral head along this wall or cortical shell.

The occurrence of arthritis in the hip joint or the fracture of the femoral neck often times requires that a prosthesis be implanted in the femur to perform this structural role. Current prosthetic designs require that the femoral head and neck be removed and the cancellous bone and marrow that make up the core of the femur are also removed, leaving only a shell made up primarily of cortical bone. A metallic prosthesis is inserted into the cavity thus formed. It is secured in place by being press fit, cemented in place, or held in place by tissue ingrowth into a porous coating on the surface of the prosthesis.

The presence of a metallic prosthesis in the femur changes the mode in which the loads are carried by the bone. This will result in the loads being carried initially by the implant and subsequently transmitted to the wall of the bone from the inside out, as opposed to always through the cortical wall as occurs with the normal femur.

The metal implants have modulus values that range from 100 to 200 GPa. In contrast, cortical bone has a modulus of approximately 20 GPa. Due to this modulus mismatch the stem of the implant carries loads that in a normal femur the cortical shell would carry. A consequence of this modified load transfer is that the cortical bone does not experience the proper mechanical environment that it requires to maintain its normal structure. Over a long enough period of time in this condition the bone will slowly resorb.

A complication that arises from bone resorption is cortical wall thinning (i.e., an increase in the size of the medullary canal of the femur). The consequences of this is that the prosthesis loses some of its support, and becomes loose and can be painful to the patient. This loss of support also can be a contributing factor to the fatigue failure of the devices.

It has been proposed that the modulus mismatch between the stem of a prosthesis and the cortical shell of the bone could be overcome to some degree by the use of a fiber reinforced composite structure whose modulus more closely conformed to that of bone. Although many such composite structures have been proposed, no composite structure has been widely used in implantable joint prosthesis.

U.S. Pat. No. 4,750,905, "Beam Construction and Method" discloses a composite femoral component for a hip joint which is constructed of a composite of carbon fiber and polysulfone. The construction includes a core formed of continuous filament fibers oriented substantially along the length of the core and embedded in a polymer matrix. The core is encased with a sheath of braided or woven filaments. The sheathed core is embedded in a polymer which fills the space of a bone cavity. The proximal end of the core is the neck of the device. The neck includes a tapered thimble which can carry the ball-like hip joint head of the prosthesis. The device disclosed in this patent does not provide for the smooth transition of forces through the device.

EPO No. 277,727 discloses a composite orthopaedic implant constructed with a polymer matrix and continuous filament carbon fiber reinforcement. A number of different polymers are disclosed including polysulfones and polyaryletherketones. The device is constructed from uniplanar sheets or prepregs which are stacked and molded to form blocks from which the devices are machined. The composite may include a sheath of continuous fiber to inhibit delamination. The sheath may be a woven or braided mantle or sock fitted over the molded prepreg. Constructions of this type have a problem in the disparity in the flexural strength and stiffness in and out of the plane of the sheets from which the product is constructed.

U.S. Pat. No. 4,892,552 and the corresponding WO No. 85/04323 also disclose a composite prosthesis made from various biocompatible polymers and reinforced with carbon fibers. The prosthesis is made of uniplanar stacked sheets molded and shaped and is similar to the prosthesis disclosed in EPO No. 0277,727.

U.S. Pat. No. 4,662,887 discloses a high modulus implantable prosthesis made from fiber reinforced polyaryletherketones.

U.S. Pat. Nos. 4,902,297, and 4,978,360 and GB2216425, disclose a composite prosthesis with a unidirectional carbon fiber core, an inner casing of braided carbon fibers, and an outer casing of an injected molded polymer.

U.S. Pat. No. 4,978,358 discloses a composite prosthesis comprising an outer component made of metal and an inner component made of a carbon fiber reinforced composite. The inner component may be made of a material of lower bending stiffness and/or higher strength than material of the outer component.

Mathys Jr., et al., Current Interdisciplinary Res., (Perren M., et al. eds.) Martinus Nyhoff, Boston (1985) pp. 371–376 and Morscher et al., "Clinical Orthopaedics and Related Research", Number 176, June 1983, pp. 77–87 disclose a hip prosthesis made from a plastic material, polyacetal, reinforced with a metallic core.

SUMMARY OF THE INVENTION

The present invention relates to a composite orthopaedic prosthesis, particularly a femoral component of a replacement hip prosthesis which avoids the problems associated with previously known composite hip prosthesis. The prosthesis of the present invention provides uniform strength and stiffness in all planes of the prosthesis. In addition, the prosthesis is better able to transmit force or load developed during normal activities between the pelvis and the cortical bone of the femur.

The composite prosthesis of the present invention minimizes the modulus mismatch of the stem portion of the component with the cortical shell of the femur. In use, the stiffness of the inner member (prosthesis) of the femur-prosthesis combination is minimized which forces the outer member (cortical shell) to carry a greater portion of the load and react closer to the normal physiological manner thereby reducing the problem of bone resorption.

The prosthesis of the present invention includes a metal core which extends from the distal end of the stem of the prosthesis to the proximal end of the stem and to the neck of the prosthesis. The proximal end of the metal core has the standard neck geometry, including a trunnion, used on standard metal hip prosthesis to allow the ball component of the prosthesis to be attached to the stem. The metal core may also include a cap which overlies and covers the proximal end of the composite shell. The cross sectional area of the metal core can be varied over the length of the stem to control the flexural properties of the stem.

The metal core is covered or encased by a composite shell. The composite shell is composed of high tensile strength filaments in a matrix of a biocompatible thermoplastic resin. The thickness of the shell may be varied from the proximal end to the distal end of stem.

The composite shell is fabricated so that the shell has substantially equal strength in all directions i.e. isotropic. This can be accomplished by arranging the high strength filaments so there are filaments substantially longitudinally oriented along the length of the stem and transverse to the length of the stem. Such fiber orientation is shown in U.S. Pat. No. 4,892,552 and EP 277,727 cited above. The preferred method of arranging the filaments is by the filament braiding techniques described in more detail below.

At the proximal end of the stem, adjacent the neck, there is an insert between the braided shell and the metal core. The insert is preferably made from a composite material, but can be made of any biocompatible material, i.e., metal or polymer. The stiffness of the insert may be selected to increase or decrease the stiffness of the proximal region of the stem as may be required for various modalities. The use of an insert also provides a method to define or vary the proximal geometry of the stem. In some configurations, the insert can be formed as an integral part of the core.

The three components of the device are assembled by bonding all three components together by heat and pressure or by adhesives or by a combination of heat and pressure and adhesives.

The three components of the device contribute attributes or benefits to the complete device which are not found in prior art hip stems, either metallic or composite.

The first benefit is the increase in the strain of the proximal cortical wall of the femur. The decreased modulus of the present stem will cause the strains to be closer to normal physiological strains. The ramifications of this is that bone resorption will be reduced and the device will be provided with a more consistent means of support. This should result in a less painful device since a gap will not develop between the device and the cortical shell of the bone. Hence, there will be no movement between the device and the bone which would be a possible source of pain to the patient.

The composite shell offers several options for device construction that do not exist in other designs. The stiffness of the device over its length can be varied in order to respond to various modalities. A less stiff proximal region in the normal stem will allow the proximal cortical shell to carry more of the load. This will result in much higher strains in the proximal bone and should eliminate proximal cortical bone resorption. A braided composite revision stem could have a stiffer proximal section than the normal stem in order to make up for the lack of cortical bone support that can occur in revision cases.

The use of a metallic neck in a composite stem results in a higher strength neck, for a fixed volume, than is possible with a fiber-resin composite. In the unsupported region of the hip joint the neck of the device is subjected to a high stress region as a result of the bending, compressive, and torsional stresses caused by normal daily activities such as rising from a chair and stair climbing. This also allows for a minimal Morse taper type femoral head to be used without any concern about the long-term behavior of the composite. A metal cap can be affixed to the core and neck which provides a solid surface to apply force to seat the stem in the medullary canal. The cap may also be an integral portion of the core.

BRIEF DESCRIPTION OF THE DRAWINGS

FIG. 2 is a cross sectional view of the prosthetic device of the present invention taken along lines 2—2 of FIG. 1.

FIG. 3 is a cross sectional view of the core of the prosthetic device taken along lines 3—3 of FIG. 2.

FIG. 4 is a side view of a mandrel used to make the prosthesis of the present invention showing an insert on the lateral side of the prosthesis.

FIGS. 4a-4d are cross sectional views of the metal core of FIG. 4 taken along lines 4A—4A, 4B—4B, 4C—4C and 4D—4D respectively in FIG. 4.

FIG. 5 is a fragmentary view of the winding of the braided sheath on the stem of the present invention.

FIG. 8 is a side view of an embodiment of a mandrel used to make the prosthesis in the present invention with an insert on the medial side.

FIGS. 8A-8D are cross sectional views of the mandrel of FIG. 8 taken along lines 8A—8A, 8B—8B, 8C—8C and 8D—SD respectively in FIG. 8.

DETAILED DESCRIPTION OF THE INVENTION

As previously indicated, the prosthesis of the present invention is particularly directed to the femoral component of an artificial hip prosthesis. It should be understood that the invention could also be used in the manufacture of other implantable prostheses, specifically those which have a stem which is implanted into a bone cavity. Implantable knee, elbow and shoulder prostheses may also have such stems. The present invention finds particular advantage for use in an implantable hip prosthesis for the reasons previously explained and will be described in reference to such hip prosthesis.

Figure 1:
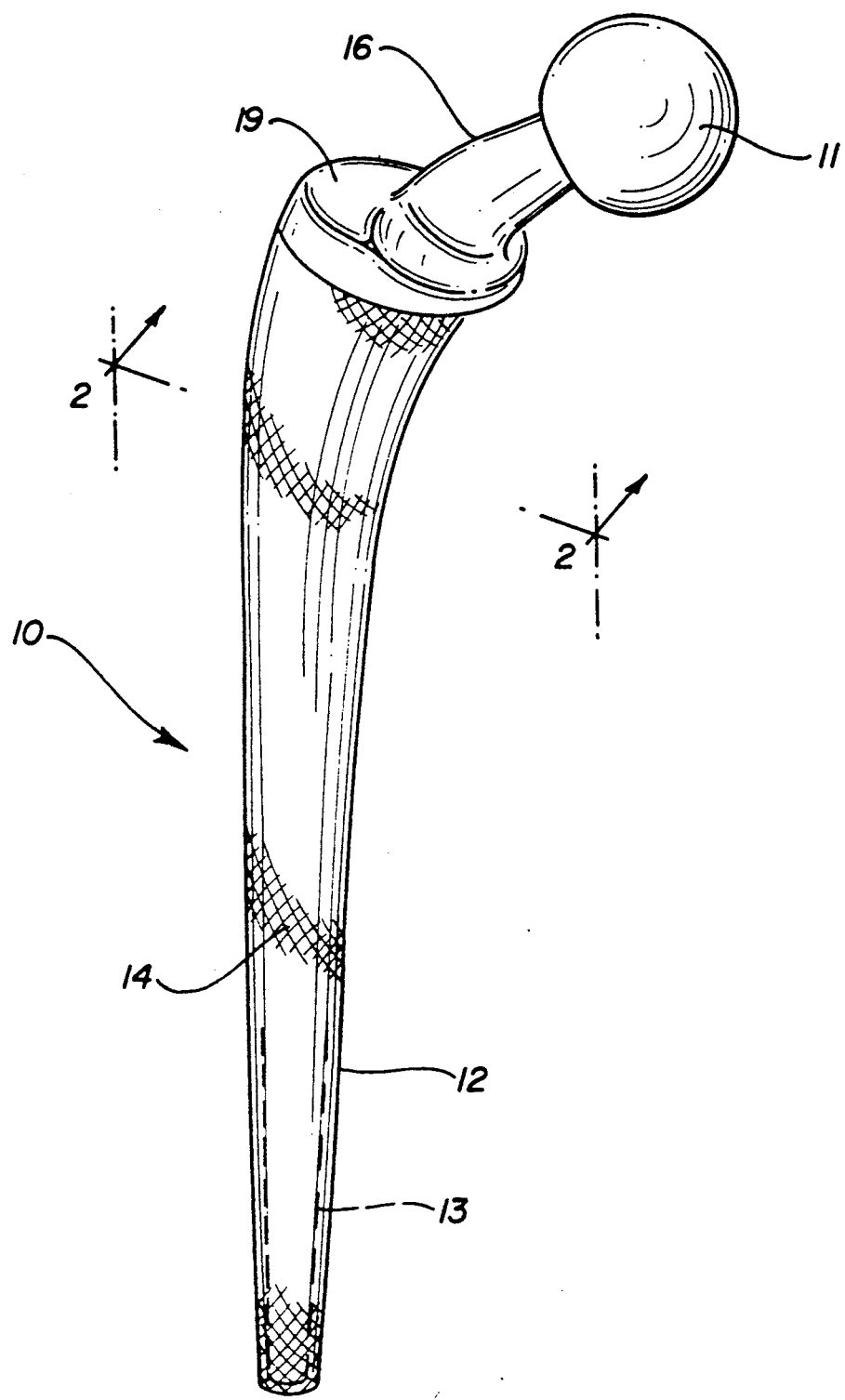
FIG. 1 is an isometric view of the prosthetic device of the present invention.

FIG. 1 shows an isometric view of the prosthesis 10 of the present invention. It should be understood that the ball 11 on neck 16 shown in FIG. 1 is a standard ball which is sized to fit into the acetabular cup component of a total hip prosthesis. Metal or ceramic balls of the types commonly used in implantable hip prostheses can be readily used with the hip stem of the present invention. Also, the acetabular cup component of a total hip prosthesis of the types commonly used with other femoral components can be used with the hip stem component of the present invention.

As shown in FIG. 2 the stem 12 of the prosthesis has an inner core 13, a composite outer shell 14 and an insert 15 adjacent the proximal end of the stem between the core 13 and the composite shell 14.

In describing the prosthesis and the method of making the prosthesis, the term "insert" describes a component of the finished prosthesis and the term "spacer" describes a fixture that is used as part of the mandrel during the manufacture of the composite shell but that is not necessarily a part of the finished prosthesis.

Figure 7:
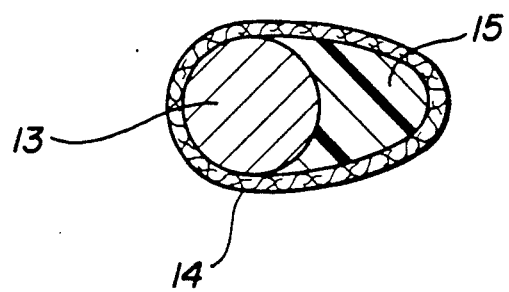
FIG. 7 is a full cross sectional view of embodiment of the invention shown in FIG. 6, taken at a position along the stem of the prosthesis shown as line 7—7 of FIG. 6.

The core 13 may be constructed of metal or a combination of metal and a polymer or a composite of polymer and reinforcing fiber. The preferred material of construction of the core is metal of the type previously used in joint prosthesis such as a cobalt-chrome alloy or a titanium alloy. The titanium alloy Ti-6A1-4V is preferred. The use of a metal core also facilitates the construction of the neck portion 16 and cap portion 19 of the stem as the metal can be machined to provide a Morse-type taper to allow the ready attachment of the ball 11 to the neck 16. The cross section of the core can be tapered or otherwise varied along the length of the stem to control the flexural properties of the stem. The metal core can be made by casting or forging depending on the material selected. It may be surface finished to the desired dimensions. The stiffness or flexural rigidity of the stem is provided by the core, the insert and the composite shell. In order to minimize the mismatch between the stiffness of the stem and the bone into which the stem is implanted, the core should provide only about 5 to 25%, preferably about 10% of the stiffness of the entire stem. The particular shape or cross sectional configuration of the core can be varied depending on the particular configuration of the finished prosthesis. Tapered rods with a circular or ovoid cross section are suitable. A core with a circular cross section shown in FIG. 7 is preferred.

The composite shell allows for the selection of the mechanical properties that are desired for a particular prosthesis, that is, the stiffness of the composite shell, (compared to the stiffness of the core) can be chosen such that the strains transmitted to the cortical shell of the femur are as close as possible to the normal physiological strains. The composite shell is a composite of a high strength fiber and a biocompatible semi-crystalline thermoplastic polymer. The high strength fiber such as carbon fiber has a strength of at least 3600 MPa and a modulus of 220-240 GPa. The carbon fibers have a diameter of less than 10 microns, usually in the range of 6 to 9 microns. The polymer may be any of the thermoplastic polymers previously proposed for use in composite orthopaedic implants. However, the use of polyaryletherketone, polyetherketone, polyetherketone ketone or polyetheretherketone offer significant advantages in environmental stability over other polymers.

The composite shell is preferably a braided structure made from a commercially available composite material of carbon fiber in a polyetheretherketone thermoplastic polymer matrix. The material is available as APC-2 from Imperial Chemical Industries PLC in a variety of different forms, i.e. unidirectional and quasi isotropic sheets, tapes and tows. The polymer and fiber reinforced devices formed from the polymer are described in U.S. Pat. Nos. 4,662,887 and 4,711,945, the disclosures of which are incorporated herein by reference. All forms mentioned above are suitable for use in the present invention. The tow is preferred. The tow and sheets are available in various widths e.g. 2 mm to 300 mm. The tape or sheet is slit to a narrow width and wound onto bobbins of the type used in a braiding machine. A width of about 2 mm is a suitable width. The particular width of tape employed is a function of the number of carriers on the braider and the desired diameter of the prosthesis and the desired fiber angle. The tape is then braided onto a mandrel which has the geometry of the desired prosthesis. The braid is applied to the mandrel one ply at a time until the desired diameter is obtained.

A carbon fiber tow impregnated with the polymer is available with variations in resin content of from 30 to 60% by volume, 24 to 52% by weight. The tow is preferred to other forms of impregnated fiber because it is more consistent in thickness and width. The fibers in the tow are also continuous and there are no ends that can split off during the braiding operation.

The plys of the impregnated carbon fiber can be laid on the mandrel at various angles to the longitudinal axis of the mandrel. A typical construction would include laying the fibers (the tape or tow) in a triaxial construction with fibers in the longitudinal direction, i.e., 0°, and other fibers in two directions symmetrical about the 0° fibers i.e. 45° in either direction. It should be understood that the angle of the fibers will change over the length of the stem as the diameter of the stem varies from the distal end to the proximal end and because of the limitations of the braiding process. The advantage of a braided shell compared to a laminated structure of the type used in previous composites such as disclosed in EPO 0277,727 is that in the laminated structure all of the fibers are parallel to each other in any given ply, while in a braided structure the fibers in any given ply are at various angles within a given ply and are interlocked and transversely isotropic. This results in a device that will flex uniformly in the medial/lateral and the anterior/posterior planes as compared to a laminated structure which would not be isotropic in both planes. It should also be understood that the thickness of the braided shell will vary with the cross section of the mandrel. That is, as the cross section and circumference of the mandrel increases, the thickness of the braided shell will decrease. This is because the same volume of fiber as tape or tow, is applied at any point along the length of the mandrel and if the circumference of the mandrel increases, the tape thickness will decrease. The cross sectional area of the braided shell is relatively constant throughout the length of the stem.

The braided structure also provides more resistance to delamination because each ply has fewer fiber ends. The stiffness of the braided shell is determined by the number of plys of the fibers in the braid and the ratio of fiber to resin in the tow or tape from which the shell is made. The stiffness in any particular direction will depend on the fiber content in the particular direction. Generally, the number of plys will vary from approximately 2 plys to 16 plys. The fiber content will be between about 40% and 70% by volume of the composite shell. The fiber orientation in the bias direction can be varied over wide angles but will be between about 30° and 75° to the longitudinal axis of the stem. The fiber orientation in the axial direction can be varied by about 10° from the longitudinal axis of the stem.

The spacer 15 acts as an addition to the mandrel to determine the outer geometry of the proximal portion of the stem. The design of the device is such that there is a significant flair in the proximal-medial contour of the stem. This geometry change can not be accomplished by using only a braided structure. The major limitation to the braiding process is that it can only apply material in a symmetric manner about the part. Therefore, creating an asymmetric or variable cross section structure with a braid alone is not possible and this change in volume of the stem has to be created in some manner other than with the braid. This volumetric change is best accomplished with the use of a spacer in the braiding process. In some constructions, the spacer can be an integral part of the core when construction allows the core to be used as the mandrel in the braiding process. In other constructions, the spacer is used only during the braiding process and removed before the core is joined to the composite shell. In such constructions, an insert is placed between the core and the shell in the finished prosthesis as will be later described.

The insert can be constructed from any one of a number of materials depending on the desired proximal stiffness. A prosthesis with a flexible proximal geometry could have a pure resin insert. A revision prosthesis with a stiffer stem in the proximal area would have a metal insert such as Cobalt-Chromium. For this type of prosthesis, the braid could be applied directly to a metal core, and the insert would be integral with the core. A third and the preferred option is to have a fiber reinforced insert that has a stiffness similar to that of the braid. However the stiffness of the insert may also be varied by changing the fabrication technique and the fiber reinforcement to correspond to a particular design.

Other alternative constructions for the insert would include making the insert out of two or more materials. The proximal portions could be made out of Titanium or cobalt chromium and the distal portion could be a composite or resin. This would result in a shifting of the load transferred to the stem to a slightly more distal location. In particular, such construction could be used for a custom device where most of the proximal calcar of the patient has resorbed and the surgeon would not desire the bone to carry much of the load.

The metal components of the device consist of a tapered Chrome-Cobalt or Titanium core and a Chrome-Cobalt or Titanium cap neck and trunnion component. These parts may be fabricated as a single piece or may be separate pieces that are welded together.

FIG. 2 shows a metal core 13 with an extension 17 machined in the proximal end of the core. The extension 17 is fitted into an opening 18 in the cap 19. The parts are then welded into a single component using electron beam or other welding techniques such as arc, laser, resistance and friction welding. Brazing and diffusion bonding may also be used to join the metal components. The cap 19 would subsequently be polished so the extension 17 would not be visible. The extension 17 is shown with a shoulder in FIG. 2 and without a shoulder in FIG. 6. The use of a shoulder on the extension 17 is optional.

The composite shell may be attached or applied directly to the metal core or formed on a mandrel. The choice of construction depends on whether the insert is a different material than the core and the configuration of the finished prosthesis. If the core is curved, e.g. when the insert is placed on the lateral side of the prosthesis as shown in FIG. 2, a core with an integral insert could not be inserted into the composite shell. In this situation the prosthesis could be constructed with a separate insert or by applying the fibers directly onto the core to form the prosthesis. The braided shell would be removed from the mandrel and a core component would be fitted into the shell in the manner later described. FIG. 4 shows a mandrel 20 with an spacer 21 in a position on the lateral side of the mandrel. The braid is applied from the smaller end of the mandrel to the larger end which is from the distal end to the proximal end of the prosthesis. A spacer 21, which is the size of the insert used in the final prosthesis, may be used during the braiding process. As indicated above, the braid varies in thickness with the diameter or circumference of the mandrel. As shown in FIGS. 4A–4D, the braid thickness is at a maximum at the smaller end of the mandrel, FIG. 4A, and decreases in thickness, FIGS. 4B and 4C, to the larger end of the mandrel FIG. 4D. The distal end portion of the mandrel is longer than the desired length of the stem for ease in processing. If the braid is applied directly to a core excess metal extending beyond the braided shell will be removed to form the desired final configuration of the prosthesis. FIG. 5 illustrates the braid positioned on the core.

Figure 6:
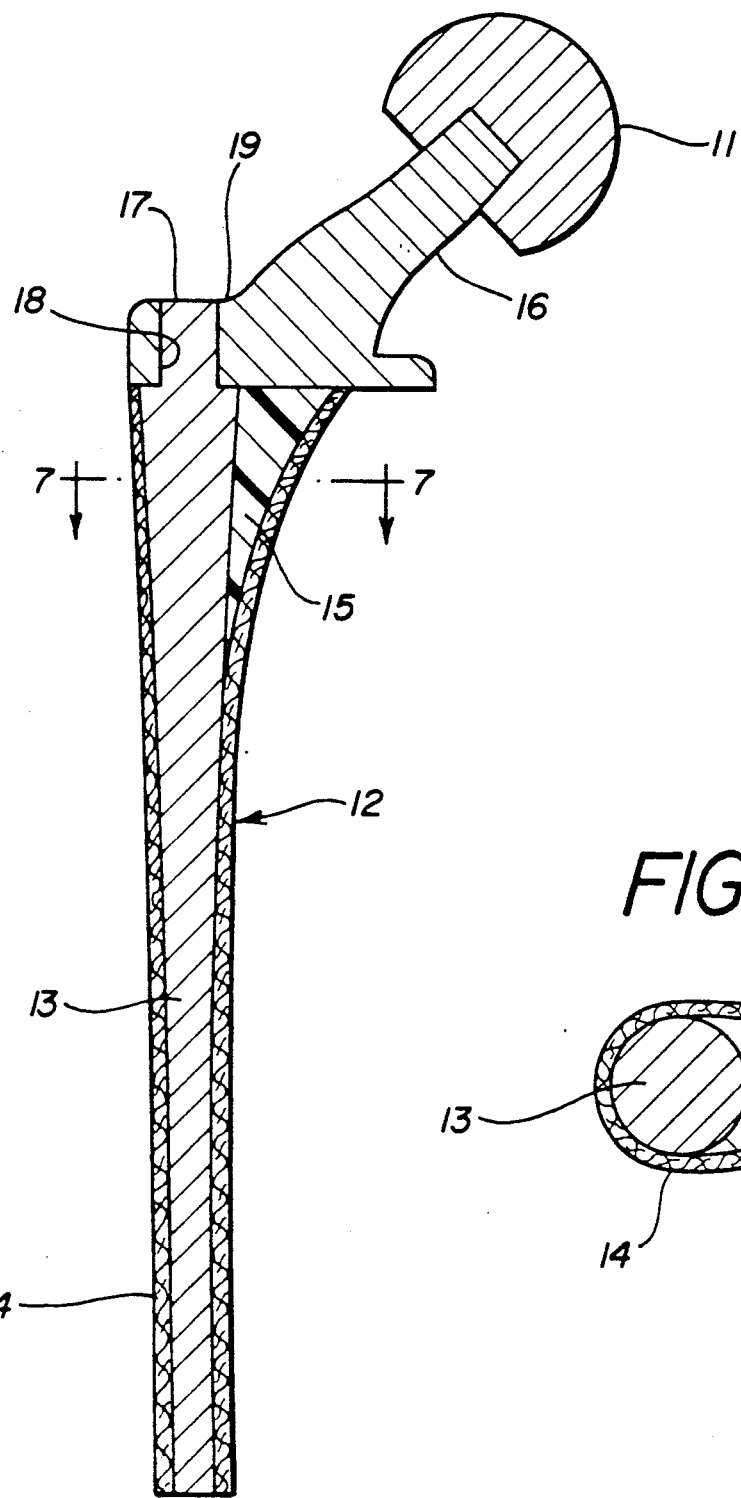
FIG. 6 is a cross sectional view of another embodiment of the present invention with an insert on the medial side of the prosthesis.

FIG. 6 shows a hip prosthesis with the insert 15 on the medial side of the prosthesis.

The cross sectional area of the metal core 13 at a position immediately adjacent the cap of the prosthesis of FIGS. 6 and 7 is circular. The cross sectional area of the core at the same position in the design shown in FIGS. 2 and 3 is ovoid or egg shaped.

FIG. 8 and FIGS. 8A-8D show a mandrel that could be used to make the prosthesis of FIG. 6 and cross sectional areas of the mandrel at different points along its length. The cross sectional area of the core in this design is always circular.

The total stem is fabricated by the following procedure: The braided shell is made by braiding over a mandrel as many plys as necessary to create the distal outer diameter. The braid may be adjusted with regard to the width of the tow being braided and the number of carriers being used to control the thickness of the individual ply, the fiber orientation within the ply and the ratio of fiber to resin in the tow in order to control the stiffness of the device. The insert may be an integral part of the mandrel or may be a separate piece affixed to the mandrel prior to braiding. The core, insert and braided shell are then assembled with a layer of thermoplastic resin applied to any metal components. The resin may be applied in the form of a piece of film, a plasma sprayed coating, or a molded coating on the metal core, or a combination of the three. The resin may either be the same as the matrix materials or miscible in the matrix material. The source of the resin may not need to be separately applied to the components but may be applied to the composite components during the composite fabrication process rather than during the joining process.

Figure 9:
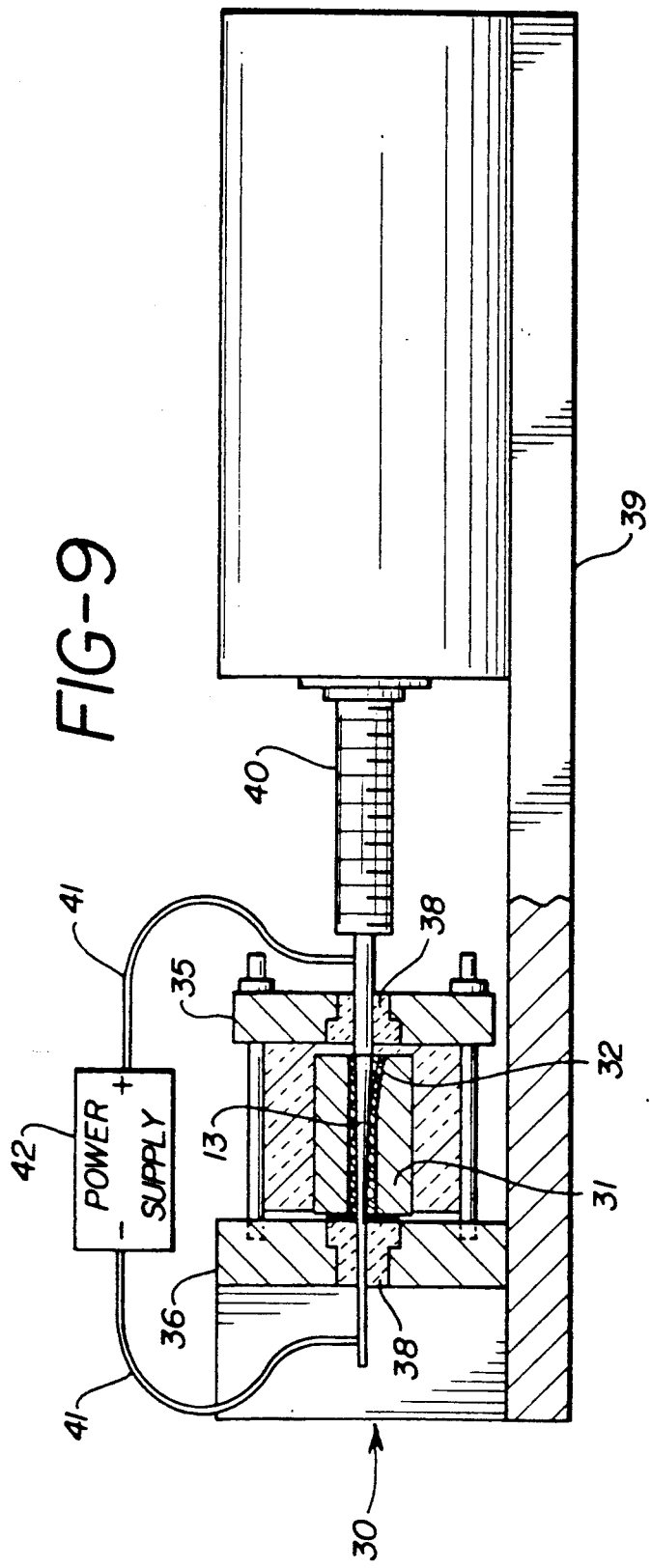
FIG. 9 is a side view, partially in section, of the apparatus used to assemble the prosthesis of the present invention.

In the assembly of the prosthesis, the braided shell is removed from the braiding mandrel and machined to dimensionally match the length of the containment mold 31 in FIG. 9, which is about the length of the finished stem. The inside taper of the composite is lightly sanded to remove any contaminant from the surface and to provide a roughened surface for the adhesive to which the adhesive will readily bond. The surface is then washed with water rinsed with a solvent such as acetone or isopropyl alcohol and air dried or oven dried to remove the residual solvents. The metal core that will be used is then sand blasted to provide a roughened surface for adhesive bonding. The core is then cleaned in an ultrasonic cleaner with a similar type of organic solvent that is used to clean the composite shell and then vapor degreased. The adhesive is then applied to either the metal core or to the inside of the composite shell or to both. The adhesive may be in the form of a thin polyetheretherketone resin film cut into a conical pattern to fit the interior of the shell. The adhesive may also be sprayed on to the core or otherwise applied to the core or the shell. If the adhesive is the form of a film, the film is also cleaned with a solvent and oven dried to remove any absorbed moisture.

The procedure to produce the composite is described in more detail below.

Figure 10:
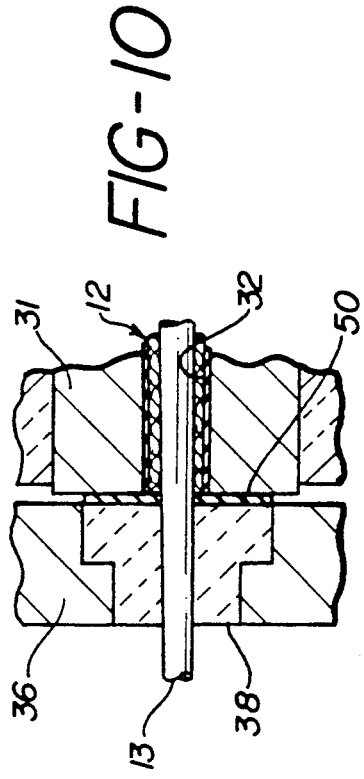
FIG. 10 is a fragmentary detail view of the apparatus of FIG. 9.

The apparatus to bond the core, insert and shell is depicted in FIGS. 9 and 10. A bonding fixture 30 contains a containment mold 31 which has a cavity 32 which corresponds in shape to the outer surface of the prosthesis. The mold 31 is held in the fixture 30 in a block 34 of insulation material. The plates 35 and 36 are joined by bolts 37 which contain the block 34. There are ceramic insulators 38 in each plate with an opening of sufficient size to allow the ends of the metal core to pass through the opening when the core-shell assembly is placed in the fixture, and when the core moves during the bonding operation.

The plates 35 and 36 are secured to a base 39. Also attached to the base 39 is a pneumatic or hydraulic cylinder with a piston 40 which can apply force to the core. An electric motor with a ball-screw actuator may be used in place of a pneumatic or hydraulic cylinder.

An electrical power supply provides current to the core which provides the necessary heat to bond the assembly.

The shell, insert and core are then assembled and placed in the end station of the bonding fixture. At the distal end of the core there is placed a seal 50, best shown in FIG. 10, to prevent the flow of the adhesive out of the interface between the core and the braided shell upon the application of heat and pressure. This seal can be made from a thin piece of ductile metal such as titanium or brass approximately 0.005-0.007 inches thick which has an opening slightly smaller than the diameter of the core at the point where the core contacts the seal. The core in contact with the seal prevents the flow of adhesive out of the mold when pressure is applied. When the components are fitted into the bonding fixture, the wires 41 from the power supply 42 are attached to both ends of the core. Electricity is then allowed to flow through the core and at the same time force is applied through the piston 40 to push the core in the direction of diminishing taper against the braided shell. The flow of electric current through the core heats the core. This bonds the shell to the core. When the bonding procedure is completed the piece is allowed to cool and the excess portions of the core are removed by cutting and the finished stem is machined to its proper shape.

EXAMPLE 1

An example of the above procedure is as follows:

A Ti-6A1-4V core and a polyetheretherketone/Carbon fiber braided shell were fitted together with a piece of polyetheretherketone film between the core and the shell. The composite shell had a hole drilled through the wall and a thermocouple was inserted until it was in contact with the polyetheretherketone film. The electrical contacts were connected to the core and a current of 75 amps was applied to the core which resulted in a measured initial heatup rate of 40° C. per minute. Concurrently a force of 2,800 Newtons was applied to the assembly. After 13 minutes the measured bond line temperature had reached 290° C. The load was gradually increased over the next 6 minutes until a load of 6,000 Newtons was obtained and the measured bond line temperature was 300° C. This condition was then held for 1 minute at which point the power was turned off and the sample was allowed to cool to room temperature under load. The bond strength of this sample was 28.1 MPa.

An example of a modified process is the following example.

EXAMPLE 2

A Ti-6A1-4V core and a polyetheretheketone-Carbon fiber braided shell were fitted together with a film of polyetheretherketone between the core and the shell. The composite shell had a hole drilled through the shell and a thermocouple was inserted until it was in contact with the polyetheretherketone film. The electrical contacts were connected to the core and a current of 45–48 amps was applied to the core which resulted in a measured initial heatup rate of 10° C. per. minute. Concurrently a force of 1800 Newtons was applied to the assembly. The temperature at the bondline reached the Tg of polyetheretheketone at 9 minutes at which time a minor deflection of the core was noted. At this point, the load was increased to 12,400 Newtons and the resulting deflection was noted. Current was increased to 75 amps and a load was adjusted during the subsequent heatup to maintain a constant deflection. When the measured bondline temperature reached 255° C., the load was then slowly increased to 6800 Newtons over a five minute period. At this point the measured bond line temperature had reached a maximum of 290° C. The current was then shut off and the part cooled to room temperature under load over a 40 minute time period. The bond strength of this sample was 25.5 MPa.

We claim:

1. A load bearing orthopaedic prosthesis comprising a stem having a distal end adapted to be inserted into a cavity formed in a bone and a proximal end opposed to the distal end;

said stem comprising an inner metal core extending substantially the length of the stem from the proximal end to the distal end of the prosthesis;

a composite shell comprising braided high strength fibers bonded with a thermoplastic resin surrounding said metal core along substantially the entire length thereof;

said metal core contributing between 5 and 25% of the total flexural stiffness of the stem at any position along the length of the stem.

2. A load bearing orthopaedic prosthesis comprising a stem having a distal end adapted to be inserted into a cavity formed in a bone and a proximal end opposed to the distal end;

said stem comprising an inner metal core extending substantially the length of the stem from the proximal end to the distal end of the prosthesis;

a composite shell comprising high strength fibers bonded with a thermoplastic resin surrounding said metal core along substantially the entire length thereof;

said composite shell comprising between 40 and 75 weight percent fiber and 25 to 60 weight percent resin;

said metal core contributing between 5 and 25% of the total flexural stiffness of the stem at any position along the length of the stem.

3. The prosthesis of claim 1 in which the metal core is tapered.

4. The prosthesis of claim 1 in which the metal core is a Ti-6Al-4V alloy.

5. The prosthesis of claim 1 in which the composite shell comprises carbon fibers and a polyetheretherketone resin.

6. The prosthesis of claim 1 further comprising an insert located at the proximal end of the prosthesis between the core and the composite shell.

7. The prosthesis of claim 6 in which the insert is made of the same material as the braided shell.

8. The prosthesis of claim 6 in which the insert is made of the same material as the metal core.

9. The prosthesis of claim 2 in which the thickness of the composite shell is greater at the distal end of the stem than the proximal end of the stem.

10. The prosthesis of claim 2 in which the fibers in the composite shell are braided and are oriented at an angle of from 30 degrees to 75 degrees to the longitudinal axis of the stem.

11. The prosthesis of claim 1 in which the flexural stiffness of the stem varies from the proximal end of the item to the distal end of the stem.

12. A load bearing orthopaedic prosthesis comprising a stem having a distal end adapted to be inserted into a cavity formed in a bone and a proximal end opposed to the distal end;

said stem comprising an inner metal core extending substantially the length of the stem from the proximal end to the distal end of the prosthesis;

a composite braided shell comprising a high strength fiber bonded with a thermoplastic resin surrounding the metal core;

an insert located at the proximal end of the prosthesis and disposed between the metal core and the composite shell; said metal core contributing between 5 and 25% of the total flexural stiffness of the stem at any position along the length of the stem.

13. The prosthesis of claim 12 in which the insert is made of the same material as the braided shell.

14. The prosthesis of claim 12 in which the insert is made of the same material as the metal core.

* * * * *

UNITED STATES PATENT AND TRADEMARK OFFICE
CERTIFICATE OF CORRECTION

PATENT NO. : 5,314,492
DATED     : May 24, 1994
INVENTOR(S): John V. Hamilton and Salvatore Caldarise It is certified that error appears in the above-identified patent and that said Letters Patent is hereby corrected as shown below:

Title page, item [75],
Inventor, Debra J. Treacy, should be deleted.

Signed and Sealed this

Thirteenth Day of December, 1994

Attest:

BRUCE LEHMAN

Attesting Officer

Commissioner of Patents and Trademarks